United States Patent [19]

Elliott

[11] Patent Number: 4,515,779

[45] Date of Patent: May 7, 1985

[54] SKIN TUMOR REMOVAL AND HEALING COMPOSITIONS AND PROCESSES

[75] Inventor: John Q. Elliott, Blytheville, Ark.

[73] Assignee: Arkansas Medical Research & Development Corporation, Blytheville, Ark.

[21] Appl. No.: 314,241

[22] Filed: Oct. 23, 1981

[51] Int. Cl.³ ..................... A61K 33/00; A61K 35/78
[52] U.S. Cl. ................................. 424/145; 424/195.1
[58] Field of Search ............................. 424/145, 195

[56] References Cited

U.S. PATENT DOCUMENTS

| | | | |
|---|---|---|---|
| 92,209 | 7/1869 | Ramsaur | 424/195 |
| 209,331 | 10/1878 | Daniel | 424/145 |
| 1,411,577 | 4/1922 | Mullins et al. | 424/145 |

*Primary Examiner*—Jerome D. Goldberg
*Assistant Examiner*—John W. Rollins, Jr.
*Attorney, Agent, or Firm*—Nelson E. Kimmelman

[57] ABSTRACT

A composition which comprises principally powdered bloodroot powdered ginger root, and zinc chloride in relatively equal parts by weight, is applied in a number of treatments to skin lesions such as epithelioma tumors. After a short time, the growth comes out and a healing ointment comprising lard, lanolin, phenol and tannic acid powder is applied to the site until healing is effected.

10 Claims, No Drawings

SKIN TUMOR REMOVAL AND HEALING COMPOSITIONS AND PROCESSES

BACKGROUND OF THE INVENTION

A. Field of the Invention

This invention relates to compositions of matter and processes and especially to ointments for removing certain types of skin cancers and healing the site of the removed growth.

B. Prior Art

Various natural substances such as herbs or roots have beeb proposed for ingestion to treat cancer as set forth in U.S. Pat. No. 114,544. Sarsaparilla, sassafras bark, bloodroot are parts of a composition described in that patent. More recent U.S. Pat. No. 4,229,437 has taught the use of a different root, namely, dried bittersweet, together with zinc chloride to form a salve which, according to the patent, removes certain types of skin growths when applied topically.

U.S. Pat. No. 1,411,577 to Mullens is an ointment for external application for unspecified conditions or diseases, there being no mention of removal of skin growths or the like. Its ingredients include bloodroot and zinc chloride as well as an equal part of metallic cobalt and some glycerine to form a paste.

Ginger has also been used for many years as an ingredient for medicines or liniments for many different medical problems such as headache, toothache, removal of blotches and pimples, and animal diseases. Such usage is shown in Schroeck U.S. Pat. No. 267,159; Ward U.S. Pat. No. 95,173; Barger U.S. Pat. No. 92,248 (cholera), Perrin U.S. Pat. No. 448,728 (panacea) and Ramsaur U.S. Pat. No. 92,209 (blotch and pimple removal).

While each of the three ingredients of the present invention have been used as components in medicines or ointments, they have never appeared together in the form which has been found by the present inventor to be an extremely effective ointment for removing certain skin growths of the malignant type.

I have discovered through repeated experimentation and treatment of human patients that if substantially equal parts, by weight, of powdered bloodroot, powdered ginger (kowlang) root, and zinc chloride are formed into a paste, allowed to stand, then applied to certain skin cancers such as epithelioma in a series of successive treatments as detailed below, the cancerous growth or lesion selectively becomes disengaged from the surrounding dermal region in a number of days and may be easily removed. After removal, I then begin treatment of the former site of the growth with a healing ointment which comprises hog lard, lanolin, liquefied phenol and tannic acid, as will be described later.

My epitheliomal cancer-removing ointment comprises approximately equal parts by weight of (1) bloodroot in its powdered form such as Penick's "Initial Line" powdered bloodroot U.S.P. distributed by S. B. Penick and Co. of New York and Chicago, (2) powdered ginger root and (3) zinc chloride. The ginger root used was manufactured by S. B. Penick and Co. in its U.S.P. form. The zinc chloride may be, for example, the U.S.P. form 1-4326 marketed by the J. T. Baker Chemical Co. of Phillipsburg, N.J.

To make this epitheliomal cancer-removing ointment, the zinc chloride is exposed to air for several days whereupon it becomes a thick liquid. It is then added to the bloodroot and ginger root and blended together to form a paste which does not run or drop. Then the paste is allowed to set for about a week or two.

When a patient with epithelioma, malignant moles or sun spots is treated, the ointment is applied with an applicator to the lesion which, at first, appears to be, externally, very small. The day after, the previously-applied ointment is removed by swabbing with a cotton-tipped applicator which has been dipped in rubbing alcohol. An additional amount of fresh growth-removing ointment is again applied to the lesion. In the days following, the treatment is repeated in the same way. These successive applications of the removing ointment result in the lesion appearing to have a progressively larger external aspect. Depending upon the original size of the lesion, the period of enlargement may range from 4-8 days, for example. When the lesion maintains dimensional stability, it usually is ready to fall out and may easily be picked out.

At this juncture, I have found that it is highly advantageous to use a second healing-promoting ointment. This ointment is made by mixing one half pound each of hog lard and lanolin (hydrous) U.S.P. grade 1-2253 such as the product distributed by the J. T. Baker Company mentioned above. To this combination 15-20 drops of liquefied phenol U.S.P. grade as distributed by J. T. Baker or Merck, for example, is added. Liquefied phenol is 89% phenol and 11% water. Then ⅓ of a teaspoon of food grade gallotannic acid powder such as 1-0380 marketed by J. T. Baker and one oz. of white beeswax U.S.P. grade such as #0207 cakes sold by Humco Laboratory of Texarkana, Tex. are added. The ingredients are put into a double boiler and heated for 30-60 minutes until the mixture becomes entirely liquid, the ingredients being continually stirred. It is then allowed to cool whereupon it solidifies and becomes a salve or ointment.

This salve is applied by the patient to the site of the former lesion twice daily. To prevent scarring, it is important to insure that no excessive phenol remains on the healing skin, so that after it is applied, it is washed off quickly with alcohol. After each three days of applying the healing salve, the patient should return to the doctor for a check-up.

EXAMPLE 1

A 62 year old white male had two epithelioma cancers; one one the nose (basal cell) which was 4 cm before and 6 cm after treatment and the second on his neck (squamous cell) which was ½ in. before and 1½ in. after treatment. The removal salve was first applied on Feb. 2, and was treated with it each consecutive day from the 2nd to the 10th. On the 16th of Feb., both lesions were out and treatment with the healing salve began. On March 3, they were healed.

EXAMPLE 2

A 52 year old white male with a basal cell on the right cheek. First treatment was March 1 and was continued through March 4th. On March 12th, the lesion was out and it was dressed with the healing ointment. It was then applied every day until April 18th, the day it was healed.

What is claimed is:

1. An ointment for treating epitheliomal growth on the human skin comprising substantially equal proportions by weight of bloodroot, ginger root and zinc chloride.

2. The ointment according to claim 1 wherein said bloodroot and ginger root are powdered and mixed with zinc chloride to form a paste.

3. The ointment according to claim 1 wherein the three named ingredients are each present in the approximate percentage ranges of 29–37% by weight.

4. A method of treating cancers of the basal cell or squamous cell on human skin comprising:
 (a) providing an ointment consisting essentially of substantially equal percentages by weight of bloodroot, ginger root and zinc chloride,
 (b) applying said ointment on said growth,
 (c) removing after a predetermined time interval the previously-applied ointment, and
 (d) repeating steps (b) and (c) in sequence a number of times until said growth appears to attain dimensional stability whereupon it is easily dislodged from the surrounding tissue.

5. The method according to claim 4 wherein said step (c) comprises applying an alcohol to the site of said growth.

6. The method according to claim 5 wherein said solvent is a rubbing alcohol.

7. The method according to claim 4 wherein each of said respective percentages is within the approximate 29–37% range.

8. The method according to claim 4 wherein said bloodroot and ginger root in powdered form are blended with zinc chloride which, by exposure to air for a predetermined time, has tended to liquefy, said blended ingredients forming said ointment then being allowed to set for at least a few days.

9. An ointment for removing epitheliomal growths on human skin made by the steps of:
 (a) exposing zinc chloride to air until it becomes a thick liquid, and
 (b) blending into said liquid a substantially equal amount by weight of powdered bloodroot and a substantially equal amount by weight of powdered ginger root to form a paste.

10. The ointment according to claim 9 wherein, after said ingredients have been blended into a paste, the ingredients are allowed to set for at least about a week before use.

* * * * *